(12) United States Patent
Claereboudt et al.

(10) Patent No.: US 8,729,508 B2
(45) Date of Patent: May 20, 2014

(54) BEAM TRANSPORT SYSTEM FOR A HADRON THERAPY FACILITY (71) Applicants: Yves Claereboudt, Nil-Saint-Vincent (BE); Christophe Wilczak, Court-Saint-Etienne (BE); Daniel Bogaert, Braine-l'Alleud (BE)

(72) Inventors: Yves Claereboudt, Nil-Saint-Vincent (BE); Christophe Wilczak, Court-Saint-Etienne (BE); Daniel Bogaert, Braine-l'Alleud (BE)

(73) Assignee: Ion Beam Applications S.A., Louvain-la-Neuve (BE)

( * ) Notice: Subject to any disclaimer, the term of this patent is extended or adjusted under 35 U.S.C. 154(b) by 0 days.

(21) Appl. No.: 13/946,210

(22) Filed: Jul. 19, 2013

(65) Prior Publication Data
US 2014/0027654 A1 Jan. 30, 2014

(30) Foreign Application Priority Data

Jul. 27, 2012 (EP) .................................... 12178382

(51) Int. Cl.
A61N 5/00 (2006.01)
G21G 5/00 (2006.01)

(52) U.S. Cl.
USPC ........ 250/492.1; 250/389; 250/394; 250/397; 250/396 R; 250/252.2; 250/423 R; 250/494.1; 250/396 ML (58) Field of Classification Search
USPC ....... 250/492.1, 492.3, 389, 394, 397, 396 R, 250/252.2, 423 R, 494.1, 396 ML
See application file for complete search history.

(56) References Cited

U.S. PATENT DOCUMENTS 5,109,162 A 4/1992 Koch et al.
2008/0116390 A1* 5/2008 Gordon et al. ......... 250/396 ML

OTHER PUBLICATIONS

European Search Report dated Oct. 17, 2012 in corresponding European Application No. 12178382.3-2305.

* cited by examiner

Primary Examiner — Jack Berman
Assistant Examiner — Meenakshi Sahu
(74) Attorney, Agent, or Firm — Finnegan, Henderson, Farabow, Garrett & Dunner, LLP (57) ABSTRACT A beam transport system for a hadron therapy facility comprises: a main beam transport line; secondary beam transport lines branching off from the main beam transport line for delivering the hadron beam into the patient treatment stations; and switching electromagnets for deviating the hadron beam from the main beam transport line into the secondary beam transport line. A discharge circuit associated with each switching electromagnet comprises a discharge accelerating circuit capable of generating a voltage opposing the counter electromotive force induced in the electromagnet coil of the switching electromagnet when the energization of the electromagnet coil producing the hadron beam deviation is interrupted, wherein this voltage stays substantially constant or increases as the current induced in the electromagnet coil decreases.

13 Claims, 4 Drawing Sheets

BEAM TRANSPORT SYSTEM FOR A HADRON THERAPY FACILITY

CROSS-REFERENCE TO RELATED APPLICATION

This application is based upon and claims the benefit of priority from prior European Application No. 12178382.3 filed on Jul. 27, 2012, the entire contents of which are incorporated herein by reference.

DESCRIPTION OF THE INVENTION

1. Technical Field

The present invention generally relates to a hadron therapy facility. It relates more particularly to a beam transport system for such a hadron therapy facility with at least two patient treatment stations.

2. Background Art

High investment costs of a hadron therapy facility require optimizing patient throughput as much as possible. A modern hadron therapy facility typically includes several patient treatment stations, which are successively supplied with a hadron beam generated in a common hadron accelerator. If it takes e.g. 10 minutes for correctly positioning a patient in a treatment station, the throughput of a hadron therapy facility with a single treatment station would be limited to 6 patients per hour. In a hadron therapy facility with 5 treatment stations it is however possible to treat up to 30 patients per hour. This means however that—in average—only 2 minutes are available for switching the hadron beam from one treatment station to the other and for performing the irradiation itself.

A beam transport system for such a multi-station hadron therapy facility typically comprises a main beam transport line into which the hadron accelerator injects a hadron beam. Secondary beam transport lines branch off from this main beam transport line for successively delivering the hadron beam into the patient treatment stations. A switching electromagnet is associated with each of these secondary beam transport lines. When this switching electromagnet is energised, its magnetic field deviates the hadron beam from the main beam transport line into the respective secondary beam transport line. Such a switching electromagnet comprises an electromagnet coil associated with a DC power source in an electromagnet energising circuit. A switching device allows for interrupting the electromagnet energising circuit, i.e. to terminate the magnetic field deviating the hadron beam, so that the latter is now guided along the main beam transport line past the respective branch-off point.

As the electromagnetic field generated by an energised switching electromagnet is quite important, opening the switching device would produce—without any further measures—an electric arc with a very high current density between the contacts of this device. In accordance with the state of the art, this discharge arc is eliminated or reduced by a fly-back diode (also called freewheeling diode) that is mounted in parallel with the coil of the switching electromagnet. This fly-back diode allows for the electromagnetic energy stored in the electromagnet to dissipate in a closed circuit, comprising as circuit resistance essentially the resistance of the electromagnet coil.

As the electromagnetic energy stored in the switching electromagnet is quite high and the characteristic R/L of the closed discharge circuit is quite low, the decay of the current in the circuit is rather slow. Thus, it can take up to 10 s until the electromagnetic field of the switching electromagnet has sufficiently decreased for safely re-establishing the beam that is to be deviated into an irradiation room located downstream of the patient treatment station in which the previous irradiation has been carried out.

Considering that the irradiation time of a patient is itself only a matter of tens of seconds, losing with every treatment already up to 10 s for the switching-off operation, is surely a matter of concern when trying to optimize patient throughput in a particle beam therapy system with several treatment stations. This is in particular true, the more patient treatment stations the hadron therapy facility has.

A first problem underlying the present invention is to increase the patient throughput in a multi-station hadron beam therapy facility.

A further problem underlying the present invention is to increase the time during which a hadron beam can be used in a multi-station hadron beam therapy facility.

SUMMARY

The invention concerns a beam transport system for a hadron therapy facility with at least two patient treatment stations, comprising: a main beam transport line into which a hadron beam is injected; a secondary beam transport line branching off from the main beam transport line for delivering the hadron beam into one of the patient treatment stations; a switching electromagnet for deviating the hadron beam from the main beam transport line into the secondary beam transport line, the switching electromagnet comprising an electromagnet coil; an energising circuit associated with the electromagnet coil for energising the latter so as to produce a hadron beam deviation from the main beam transport line into the secondary beam transport line; a switching device for interrupting the energisation of the electromagnet coil producing the hadron beam deviation; and a discharge circuit capable of dissipating the electromagnetic energy stored in the switching electromagnet, when the energisation of the electromagnet coil is interrupted. In accordance with a first aspect of the invention, the discharge circuit comprises a discharge accelerating circuit capable of generating a voltage opposing the counter electromotive force induced in the electromagnet coil when the energisation of the electromagnet coil producing the hadron beam deviation is interrupted, wherein the voltage stays substantially constant or increases as the current induced in the electromagnet coil decreases.

Such a discharge accelerating circuit accelerates the decay of the current induced in the electromagnet coil and thereby the decay of the residual electromagnetic field in the switching electromagnet that is de-energised. Accelerating the decay of the electromagnetic field of a de-energised switching electromagnet substantially reduces the waiting time for safely re-injecting the hadron beam into the beam transport system. Hence, the time during which a hadron beam can be effectively used in a multi-station hadron beam therapy facility is increased, which allows for an increased patient throughput.

A constant voltage provides a constant contribution to the decay rate of the induced current. However, it may also be of advantage to increase the voltage as the current induced in the electromagnet coil decreases, thereby increasing the contribution of the voltage to the decay rate at smaller decay currents. Indeed, as the decay rate also includes a resistive component that is proportional to the instantaneous value of the induced current, i.e. a component which diminishes with the current, increasing the voltage as the current induced in the electromagnet coil decreases allows compensating for the diminishing resistive component of the decay rate.

In conclusion, it will be appreciated that the invention provides a simple measure for improving patient throughput in multi-station hadron therapy facilities, by efficiently reducing the waiting time for safely re-injecting the hadron beam into the beam transport system, when switching the hadron beam from one treatment station to the other.

It may be of advantage if the discharge accelerating function of the discharge accelerating circuit only starts when the current induced in the electromagnet coil drops below a certain value. At the beginning, the resistive component of the decay rate, which is proportional to the instantaneous value of the induced current, still warrants a rapid decay of the magnetic field. This resistive decay rate diminishes however as the induced current decreases. Consequently, the discharge accelerating circuit gets more efficient if the current induced in the electromagnet coil has already dropped below a certain value. As the costs of the discharge accelerating circuit normally increase with the power to be absorbed, it is consequently of interest to start the discharge accelerating function of the discharge accelerating circuit only when the current induced in the electromagnet coil has already dropped below a certain value.

A first embodiment of the discharge accelerating circuit comprises a power source capable of generating an electromotive force opposing the counter electromotive force induced in the electromagnet coil when the energisation of the electromagnet coil is interrupted. This solution allows most probably for achieving the best results in terms of discharge acceleration, but necessitates an auxiliary power source, which may not be the most cost efficient solution.

A second embodiment of the discharge accelerating circuit comprises a Zener diode, wherein the breakdown voltage of the Zener diode opposes the counter electromotive force induced in the electromagnet coil when the energisation of the electromagnet coil is interrupted. This solution allows for achieving good results in terms of discharge acceleration if the breakdown voltage of the Zener diode is sufficiently high. However, as the power to be absorbed in the Zener diode is rather high, it is presently rather difficult to find a suitable Zener diode at reasonable costs.

It may be of advantage if the discharge accelerating circuit comprises at least two Zener diodes mounted in parallel or in series. These solutions allow for reducing the power to be absorbed in a single Zener diode. The parallel solution is generally preferred. For the serial solution, it must be possible to replace a Zener diode with a breakdown voltage $V_{DZ}$ with n Zener diodes with a reduced breakdown voltage of $V_{DZ}/n$.

A third embodiment of the discharge accelerating circuit further comprises a current sensitive bypass circuit mounted in parallel with the Zener diode, respectively the Zener diodes, the current sensitive bypass circuit bypassing the decay current around the Zener diode, respectively the Zener diodes, until this current drops below a certain value. In this solution the current sensitive bypass circuit is used to "start" the Zener diode(s) only when the current induced in the electromagnet coil has already dropped below a certain value. Thereby the Zener diode has to absorb a reduced power in comparison to a Zener diode through which the initial decay current flows.

A further embodiment of the discharge accelerating circuit comprises: a first circuit including a first Zener diode and a first current sensitive bypass circuit mounted in parallel with the first Zener diode, wherein the first current sensitive bypass circuit bypasses the decay current around the first Zener diode until this decay current drops below a certain value $I_1$; and at least one second circuit mounted in series with the first circuit and including a second Zener diode and a second current sensitive bypass circuit mounted in parallel with the second Zener diode, wherein the second current sensitive bypass circuit bypasses the decay current around the second Zener diode until this decay current drops below a certain value $I_2 < I_1$. It will be appreciated that this relatively simple and cost efficient embodiment allows increasing the voltage as the current induced in the electromagnet coil decreases, thereby compensating—at least partially—a decrease of the resistive component of the decay rate.

A fly-back diode is advantageously mounted in series with the discharge accelerating circuit. If necessary, the fly-back diode warrants that no energising current flows through the discharge accelerating circuit, but that the induced electromagnetic field decay current may flow through the discharge accelerating circuit.

A third embodiment of the discharge accelerating circuit comprises: a first branch including a Zener diode; a second branch connected in parallel with the first branch, the second branch including a high-power MOSFET; and an OP amplifier controlling the gate of the MOSFET so that the breakdown voltage $V_{ZD}$ of the Zener diode defines the drain-source voltage $V_{DS}$ of the MOSFET; wherein this discharge accelerating circuit is designed so that the current flowing through the first branch is small in comparison to the current flowing through the second branch. This circuit allows for achieving a very cost efficient solution with presently available circuit components.

In a preferred embodiment of the beam transport system, a single power source is associated with several electromagnet coils; a switching device is connected between the power source and the electromagnet coils for selectively disconnecting one electromagnet coil from the power source and connecting another electromagnet coil to the power source; and a discharge accelerating circuit is associated with each of the electromagnet coils.

In a preferred embodiment of the beam transport system, the power source has a voltage output adjustable between a maximum value and a steady state value; the beam transport system further includes a controller setting the voltage of the power source to its maximum value when the power source is newly connected to one of the electromagnet coils and reduces it to its steady state value as soon as the current in the electromagnet coil reaches its steady state value. This solution allows for reducing—at relatively low costs—the time necessitated for building up the required electromagnetic field in a switching magnet.

The energising circuit and the discharge accelerating circuit are advantageously designed so that the time interval required for reducing to zero the decay current induced in the electromagnet coil associated with a first patient treatment station when its energising circuit is interrupted is substantially equal to the time interval required for establishing a desired working current in the electromagnet coil associated with a second patient treatment station, when the hadron beam is to be switched from the first patient treatment station into the second treatment station.

BRIEF DESCRIPTION OF THE DRAWINGS

The afore-described and other features, aspects and advantages of the invention will be better understood with regard to the following description of several embodiments of the invention with reference to the attached drawings, wherein.

DETAILED DESCRIPTION

It will be understood that the following description (and the drawings to which it refers) describe by way of example several embodiments of the claimed subject matter for illustration purposes. They shall not limit the scope, nature or spirit of the claimed subject matter.

Figure 1:
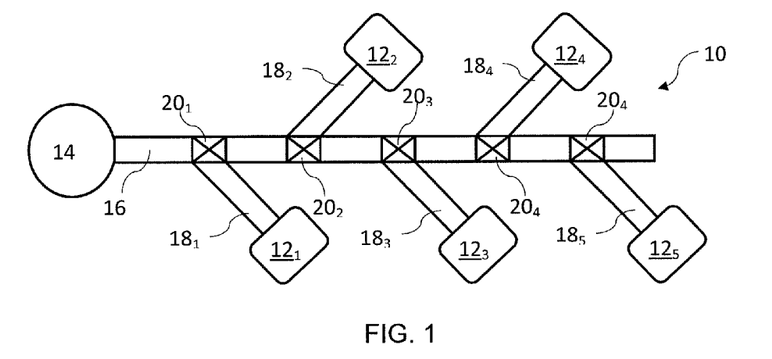
FIG. 1: is a schematic diagram illustrating a beam transport system for a hadron therapy facility with five patient treatment stations.

The diagram of FIG. 1 schematically illustrates the layout of a beam transport system, globally identified with reference number 10, for a hadron therapy facility with five patient treatment stations (or treatment rooms) $12_1$, $12_2$, $12_3$, $12_4$, $12_5$. Reference number 14 identifies a hadron accelerator (e.g. a cyclotron or a synchrotron) connected to the beam transport system 10.

The hadron beam produced by the hadron accelerator 14 is injected in a main beam transport line 16. Secondary beam transport lines $18_1$, $18_2$, $18_3$, $18_4$, $18_5$ branch off from this main beam transport line 14 for delivering the hadron beam into the patient treatment stations $12_1$, $12_2$, $12_3$, $12_4$, $12_5$, where it is injected into an equipment used to irradiate the patient as e.g. a rotating gantry or a fixed beam treatment device (not shown). Each of these beam transport lines 16, $18_1$, $18_2$, $18_3$, $18_4$, $18_5$ comprises—in a manner known per se—a beam transport tube and a series of powerful electromagnets (not shown) capable of focussing the hadron beam and routing it through the beam transport tube.

Reference numbers $20_1$, $20_2$, $20_3$, $20_4$, $20_5$ identify switching electromagnets, whose function is to switch the hadron beam from the main beam transport line 16 into the respective secondary beam transport line $18_1$, $18_2$, $18_3$, $18_4$, $18_5$ with which they are associated. Each of these switching electromagnets $20_1$, $20_2$, $20_3$, $20_4$, $20_5$ comprises an electromagnet coil (or coil system) $22_1$, $22_2$, $22_3$, $22_4$, $22_5$. When the electromagnet coil $22_i$ is energised, the respective switching electromagnet $20_i$ generates a strong magnetic field deviating the hadron beam from the main beam transport line 16 into the secondary beam transport line $18_i$, with which the respective switching electromagnet $20_i$ is associated.

Figure 2:
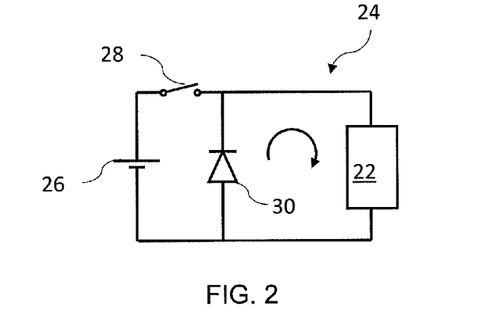
FIG. 2: is a schematic circuit diagram showing a prior art energising/discharge circuit of a switching electromagnet.

FIG. 2 shows a prior art energising circuit 24 comprising the aforementioned electromagnet coil (or coil system) 22, a DC power source 26 and a switching device 28 for interrupting the energising circuit 24 (i.e. for suppressing the electromotive force in the energising circuit 24 which generates the magnetic field deviating the hadron beam from the main beam transport line 16 into the secondary beam transport line $18_i$). Reference number 30 identifies a fly-back (or freewheeling) diode. The latter forms with the electromagnet coil 22 a discharge circuit, wherein—when the energisation of the electromagnet coil 22 is interrupted by opening the switching device 28—a current I is induced in the discharge circuit, which opposes the decay of the electromagnetic field stored in the switching electromagnet 20. As long as this residual electromagnetic field is capable of substantially influencing the trajectory of the hadron beam, it is not safe to re-inject this hadron beam into the main beam transport line 14. Consequently, the time required for a sufficient decay of the electromagnetic field in a switching electromagnets $20_i$ is a time overhead during which the hadron beam is not available for the next treatment station $12_{i+1}$.

If R is the resistance in the discharge circuit, L is the inductance in the discharge circuit, and $V_D$ is the voltage drop at the fly-back diode (for I>0, one may assume that $V_D$ is constant), the electromagnetic field decay current I in the prior art circuit of FIG. 2 is determined by the following differential equation:

$$-L \cdot \frac{dI}{dt} = R \cdot I + V_D$$

As R is typically small (a typical value for R would e.g. be 30 mΩ), L is large (a typical value for L would e.g. be 30 mH) and $V_D$ is small, the current decay rate (−dI/dt) in the discharge circuit is relatively small considering the high currents used in these magnets (>300 A).

Figure 3:
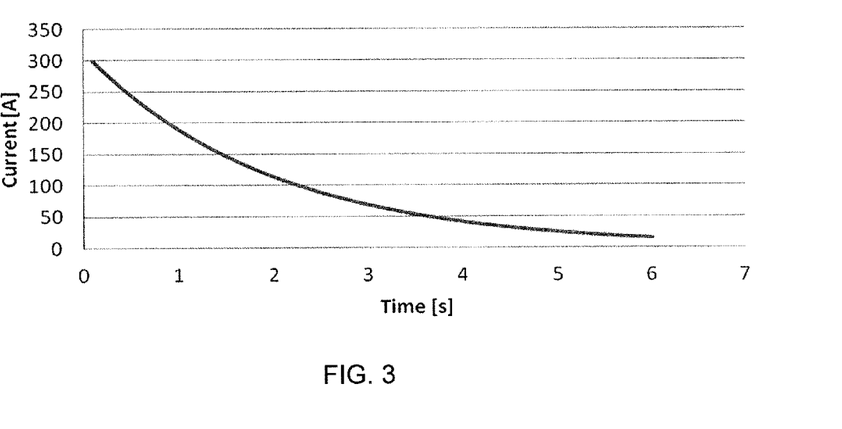
FIG. 3: is a schematic diagram showing the electromagnetic field decay current in the prior art discharge circuit of FIG. 2.

A typical curve for the electromagnetic field decay current I in the discharge circuit of FIG. 2 is shown in FIG. 3. It will be noted that it takes more than 6 s for the current induced in the in the discharge circuit to drop below 10 A.

It will further be noted that simply increasing the resistance R in the discharge circuit is not an efficient solution for accelerating the decay of the electromagnetic field in the switching electromagnet 20. Indeed, increasing R would increase the value of the counter electromotive force (−L·dI/dt) induced in the discharge circuit, thereby increasing the electric potential difference between the contacts of the switching device 28, when the latter opened. Furthermore, the contribution of the resistance R to the current decay rate (−dI/dt) is proportional to the instantaneous value of current I, i.e. its contribution diminishes as the current I diminishes.

Figure 4:
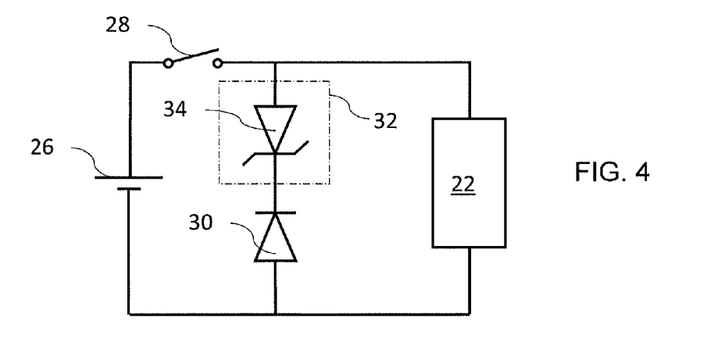
FIG. 4: is a schematic circuit diagram of a first embodiment in accordance with the invention of an energising/discharge circuit of a switching electromagnet.

FIG. 4 shows a first embodiment of a discharge circuit with a first embodiment of a discharge accelerating circuit 32. The latter is mounted in series with the fly-back diode 30 and comprises a high power Zener diode 34. In this discharge circuit of FIG. 4, the breakdown voltage of the high power Zener diode 34, which is generated by the current passing through the fly-back diode 30, opposes the counter electromotive force induced in the electromagnet coil 22 when the energisation of the latter is interrupted.

If R is the resistance in the discharge circuit', L is the inductance in the discharge circuit, $V_D$ is the voltage drop at the fly-back diode 30 and $V_{ZD}$ is the breakdown voltage of the high power Zener diode 34, the electromagnetic field decay current I is determined by following differential equation:

$$-L \cdot \frac{dI}{dt} = R \cdot I + V_D + V_{ZD}$$

The current decay rate (−dI/dt) in the discharge circuit is increased by the constant term $V_{ZD}/L$.

Expressed in more general terms, the discharge circuit of FIG. 4 comprises a discharge accelerating circuit 32 that generates a constant voltage $V_{ZD}$ opposing the counter electromotive force induced in the electromagnet coil $22_i$ when its energisation is interrupted.

Figure 5:
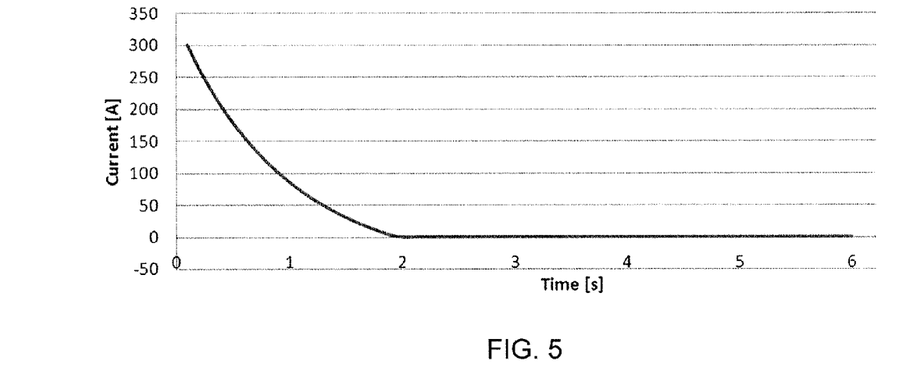
FIG. 5: is a schematic diagram showing the electromagnetic field decay current in the prior art discharge circuit of FIG. 4.

A typical curve for the electromagnetic field decay current I in the discharge circuit of FIG. 4 is shown in FIG. 5 (the breakdown voltage $V_{ZD}$ of the high power Zener diode is 15 V, and R, L and $V_D$ have the same values as in FIG. 2). It will be noted that it only takes about 2 s for the current in the discharge circuit' to drop to 0 A. Consequently, in the discharge circuit of FIG. 4, the discharge accelerating circuit 32 reduces by about 70% the time required before the decaying electromagnetic field in the de-energised switching electromagnet 20 is sufficiently weak for safely injecting the hadron beam again into the beam transport system 10.

It will however be noted that in the discharge circuit of FIG. 4 the high power Zener diode 34 has to dissipate a considerable energy, corresponding more precisely to the product $V_{ZD} \cdot I$ over the time during which this power is dissipated, i.e. about 3 kJ in a couple of seconds. A Zener diode 34 capable of dissipating more than 3 kJ is presently not easy to find and would moreover be very expensive. To reduce the power for which the Zener diode is to be designed, the discharge accelerating circuit 32 may e.g. comprise several Zener diodes mounted in parallel.

Figure 6:
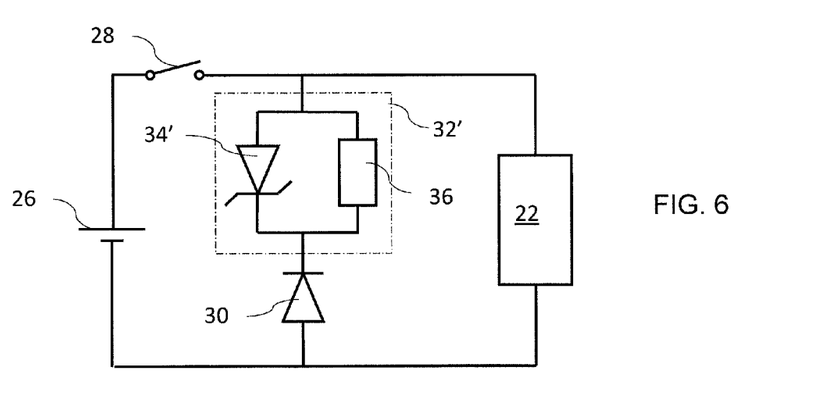
FIG. 6: is a schematic circuit diagram of a second embodiment in accordance with the invention of an energising/discharge circuit of a switching electromagnet.

FIG. 6 shows a second embodiment of a discharge circuit with a second embodiment of a discharge accelerating circuit 32'. The latter comprises a high power Zener diode 34' mounted in parallel with a current sensitive bypass circuit 36. This current sensitive bypass circuit 36 bypasses the decay current around the Zener diode 34' until this current drops below a certain value $I_1$. Such a current sensitive bypass circuit 36 may e.g. comprise a resistor transforming the current into voltage, an operational amplifier detecting a voltage level and a relay opening the bypass circuit. As soon as the decay current falls below this preset value $I_1$, the bypass circuit 36 opens. The decay current now flows through the Zener diode 34', generating the breakdown voltage of the high power Zener diode 34'. It will be noted that the Zener diode 34' has to be dimensioned for absorbing a power of $(I_1 \cdot V_{ZD})$, which may be several times lower than the power for which the Zener diode 34' in FIG. 4 has to be designed. To still further reduce the current for which the Zener diode 34' is to be designed, one may connect several Zener diodes in parallel with the bypass circuit 36.

Figure 7:
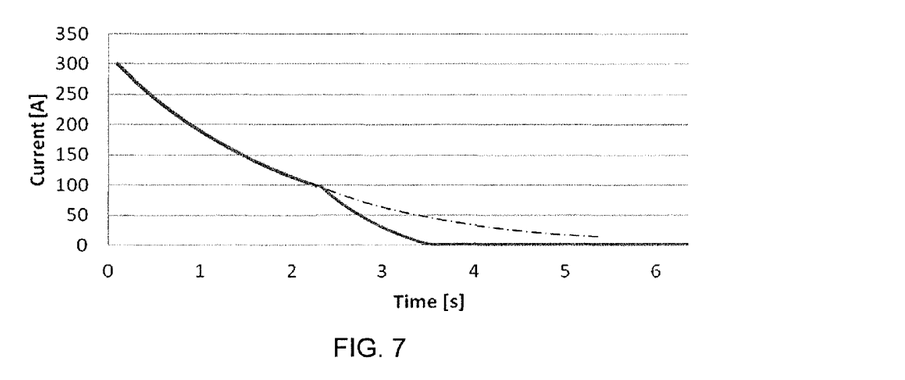
FIG. 7: is a schematic diagram showing the electromagnetic field decay current in the prior art discharge circuit of FIG. 6.

A typical curve for the electromagnetic field decay current I in the discharge circuit of FIG. 6 is shown in FIG. 7 (the breakdown voltage $V_{ZD}$ of the high power Zener diode is 15 V; the Zener diode is switched into the circuit when the current has dropped to 100 A; and and R, L and $V_D$ have the same values as in FIG. 2). It will be noted that it only takes about 3.5 s for the current in the in the discharge circuit to drop to 0 A. Consequently, discharge circuit of FIG. 6 allows for reducing by about 50% the time required before the decaying electromagnetic field in the de-energised switching electromagnet 20 is sufficiently low for safely injecting the hadron beam again into the beam transport system 10. It is to be noted that this embodiment dissipates much less energy in the diode than the previous embodiment as most of the energy stored in the magnet is dissipated within the magnet (e.g. 750 J).

Figure 8:
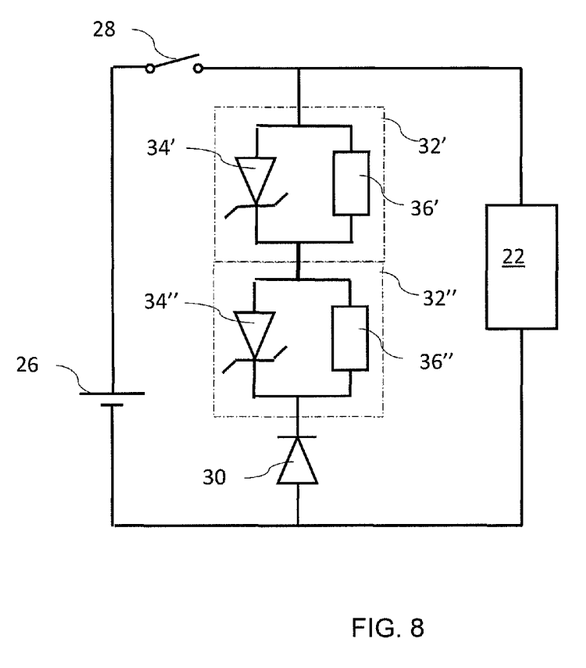
FIG. 8: is a schematic circuit diagram of a third embodiment in accordance with the invention of an energising/discharge circuit of a switching electromagnet.

FIG. 8 shows an embodiment of a discharge circuit with a discharge accelerating circuit 32', 32" capable of generating a voltage that increases as the current induced in the electromagnet coil 22 decreases. This discharge circuit comprises two discharge accelerating circuit 32', 32" as shown in FIG. 6, which are mounted in series. Each of these circuits 32', 32" comprises high power Zener diode 34', 34" mounted in parallel with a current sensitive bypass circuit 36', 36". First, both bypass circuits 36', 36" are closed. As soon as the decay current falls below a preset value $I_1$, the bypass 36' of the first Zener diode 34' opens, whereby the decay current now flows through the first Zener diode 34' generating the breakdown voltage $V_{ZD1}$ of the latter. The bypass 36" of the second Zener diode 34" stays closed until the decay current drops below a preset value $I_2$ ($<I_1$) and then opens. The decay current now flows through the second Zener diode 34", generating the breakdown voltage $V_{ZD2}$ of the latter. It follows that if the decay current drops below $I_2$, the voltage opposing the counter electromotive force induced in the electromagnet coil 22 increases from $V_{ZD1}$ to $V_{ZD1}+V_{ZD2}$. It is to be noted that in this embodiment, the second Zener diode 34" has to dissipate less energy than the first Zener diode 34'.

Figure 9:
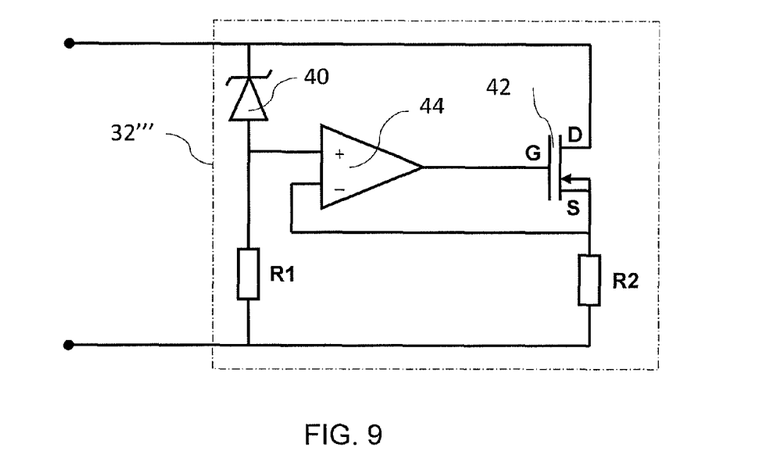
FIG. 9: is a schematic circuit diagram of a fourth embodiment in accordance with the invention of an energising/discharge circuit of a switching electromagnet.

FIG. 9 shows a fourth embodiment of a discharge circuit with a discharge accelerating circuit 32'''. The latter comprises in a first branch a low power Zener diode 40 mounted in series with a resistor R1, which limits the current flowing through the low or medium power Zener diode 40 and thereby the power dissipated in the latter. A second branch comprises an n-channel-depletion-type high-power MOSFET 42 mounted in series with a resistor R2 (<<R1). An OP amplifier 44 compares the voltage drop at the low power Zener diode 40 and the drain-source voltage VDS of the MOSFET 42 to set the MOSFET's gate voltage. It follows that the breakdown voltage VZD of the low power Zener diode 40 defines the drain-source voltage VDS of the MOSFET 42. As R2<<R1, the current in this second branch is much bigger than the current in the first branch, so that most of the electromagnetic power stored in the switching electromagnet 20 will be dissipated in the second branch. It will be appreciated that the high-power MOSFET 42 required for the discharge accelerating circuit 32" is by far less expensive than a high-power Zener diode capable of dissipating the same power.

Figure 10:
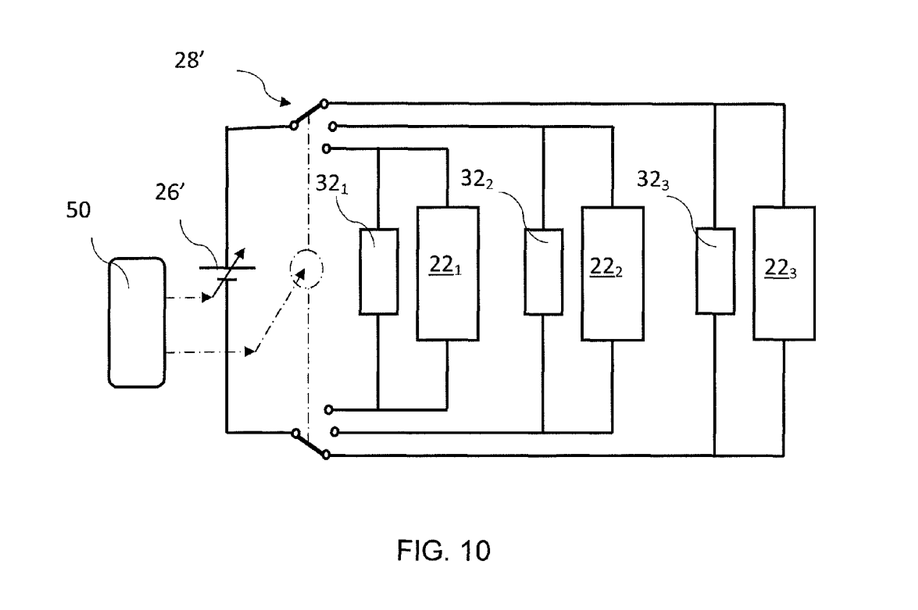
FIG. 10: is a schematic diagram illustrating a switching device for three switching electromagnets in a hadron therapy system in accordance with the present invention.

FIG. 10 shows an energising/discharge circuitry for three switching electromagnets represented by their electromagnet coils $22_1$, $22_2$, $22_3$. Each of these electromagnet coils $22_1$, $22_2$, $22_3$ is equipped with a discharge branch comprising a discharge accelerating circuit $32_1$, $32_2$, $32_3$. Reference 26' identifies a common DC power source, which may be selectively connected by a 2-deck selector switch 28' to one of the electromagnet coils $22_1$, $22_2$, $22_3$.

The switching operation is governed by a controller 50. As the controller 50 issues a signal to the selector switch 28' to switch to another position—thereby interrupting the energisation of one electromagnet coil $22_i$ and starting the energisation of another electromagnet coil $22_j$—it simultaneously issues a signal to the DC power source 26' to temporarily increase its voltage to a multiple of the steady-state voltage applied to the electromagnet coil $22_j$ for deviating the hadron beam into the respective secondary beam transport line $18_j$. This temporarily increased starting voltage shortens the time required for building up the required magnetic field in the switching electromagnet magnet $20_j$. The current in the electromagnet coil $22_i$ will exponentially decrease to 0 A during a time interval t1, which is shortened by the discharge accelerating circuit $32_i$ integrated into the discharge circuit of the electromagnet coil $22_i$. The current in the electromagnet coil $22_j$ will exponentially increase to its steady state value $I_j$ during a time interval t2, which is shortened by the controller 50 temporarily increasing the voltage of the DC power source 26'. In an optimized system, t1 and t2 are substantially equal. Due to the much higher costs involved with the discharge accelerating circuits $32_i$, t1 will generally determine the time overhead during which the hadron beam is not available for the next treatment station $12_j$.

| Reference signs list | | | |
|---|---|---|---|
| 10 | beam transport system | 30 | fly-back diode |
| $12_i$ | patient treatment stations | 32, 32', 32", 32''' | discharge accelerating circuit |
| 14 | hadron accelerator | | |
| 16 | main beam transport line | | |
| | | 34 | high power Zener diode |
| $18_i$ | secondary beam transport lines | 34' 34" | |
| $20_i$ | switching electromagnets | 36, 36', | current sensitive bypass circuit |
| $22_i$ | electromagnet coil | 36" | |
| 24 | energising circuit | 40 | low or medium power Zener diode |
| 26 | DC power source | | |
| 26' | common DC power source | 42 | n-channel-depletion-type high-power MOSFET |
| 28 | switching device | | |
| 28' | 2-deck selector switch | 44 | OP amplifier |
| | | 50 | controller |

What is claimed is:

1. A beam transport system for a hadron therapy facility with at least two patient treatment stations, comprising:
   a main beam transport line into which a hadron beam is injected;
   a secondary beam transport line branching off from said main beam transport line for delivering said hadron beam into one of said patient treatment stations;
   a switching electromagnet for deviating said hadron beam from said main beam transport line into said secondary beam transport line, said switching electromagnet comprising an electromagnet coil;
   an energising circuit associated with said electromagnet coil for energising the latter so as to produce a hadron beam deviation from said main beam transport line into said secondary beam transport line; and
   a discharge circuit capable of dissipating the electromagnetic energy stored in the switching electromagnet, when the energization of said electromagnet coil is interrupted;
   wherein said discharge circuit comprises a discharge accelerating circuit capable of generating a voltage opposing the counter electromotive force induced in the electromagnet coil when the energization of said electromagnet coil producing said hadron beam deviation is interrupted, wherein said voltage stays substantially constant or increases as the current induced in the electromagnet coil decreases.

2. The beam transport system as claimed in claim 1, wherein the discharge accelerating function of said discharge accelerating circuit only starts when the current induced in the electromagnet coil drops below a certain value.

3. The beam transport system as claimed in claim 1, wherein said discharge accelerating circuit comprises a power source capable of generating an electromotive force opposing the counter electromotive force induced in the electromagnet coil when the energization of said electromagnet coil is interrupted.

4. The beam transport system as claimed in claim 1, wherein said discharge accelerating circuit comprises a Zener diode, and the breakdown voltage of the Zener diode opposes the counter electromotive force induced in the electromagnet coil when the energization of said electromagnet coil is interrupted.

5. The beam transport system as claimed in claim 4, wherein said discharge accelerating circuit comprises at least two Zener diodes mounted in parallel.

6. The beam transport system as claimed in claim 4, wherein said discharge accelerating circuit comprises at least two Zener diodes mounted in series.

7. The beam transport system as claimed in claim 4, wherein said discharge accelerating circuit further comprises a current sensitive bypass circuit mounted in parallel with said Zener diode, respectively said Zener diodes, said current sensitive bypass circuit bypassing the decay current around said Zener diode, respectively said Zener diodes, until this current drops below a certain value.

8. The beam transport system as claimed in claim 1, wherein said discharge accelerating circuit comprises:
   a first circuit including a first Zener diode and a first current sensitive bypass circuit mounted in parallel with said first Zener diode, said first current sensitive bypass circuit bypassing the decay current around said Zener diode until this current drops below a certain value $I_1$; and
   a second circuit mounted in series with said first circuit and including a second Zener diode and a second current sensitive bypass circuit mounted in parallel with said second Zener diode, said second current sensitive bypass circuit bypassing the decay current around said second Zener diode until this decay current drops below a certain value $I_2 < I_1$.

9. The beam transport system as claimed in claim 4, further comprising a fly-back diode mounted in series with said discharge accelerating circuit.

10. The beam transport system as claimed in claim 1, wherein said discharge accelerating circuit includes:
    a first branch including a Zener diode;
    a second branch connected in parallel with said first branch, said second branch including a high-power MOSFET; and
    an amplifying circuit controlling the gate of the MOSFET so that the breakdown voltage $V_{ZD}$ of the Zener diode defines the drain-source voltage $V_{DS}$ of the MOSFET;
    wherein said discharge accelerating circuit is further designed so that the current flowing through said first branch is small in comparison to the current flowing through said second branch.

11. The beam transport system as claimed in claim 1, wherein:
    a single power source is associated with several electromagnet coils;
    a switching device is connected between said power source and said electromagnet coils for selectively disconnecting one electromagnet coil from said power source and connecting another electromagnet coil to said power source; and
    a discharge accelerating circuit is associated with each of said electromagnet coils.

12. The beam transport system as claimed in claim 1, wherein said power source has a voltage output adjustable between a maximum value and a steady state value; said beam transport system further including a controller setting the voltage of said power source to its maximum value when said power source is newly connected to one of said electromagnet coils and reducing it to its steady state value as soon as the current in said electromagnet coil reaches its steady state value.

13. The beam transport system as claimed in claim 1, wherein said energising circuit and said discharge accelerating circuit are designed so that the time interval required for reducing to zero the decay current induced in the electromagnet coil associated with a first patient treatment station, when its energization is interrupted, is substantially equal to the time interval required for establishing a desired working current in the electromagnet coil associated with a second patient treatment station, when the hadron beam is to be switched from said first patient treatment station into said second treatment station.

* * * * *